United States Patent [19]

Erickson

[11] 4,424,247

[45] Jan. 3, 1984

[54] ABSORBENT POLYMER-FIBER COMPOSITES AND METHOD FOR PREPARING THE SAME

[75] Inventor: Robert E. Erickson, Midland, Mich.

[73] Assignee: The Dow Chemical Company, Midland, Mich.

[21] Appl. No.: 319,538

[22] Filed: Nov. 9, 1981

[51] Int. Cl.$^3$ ............................................. B32B 3/10
[52] U.S. Cl. .................................. 428/138; 264/115; 264/116; 264/140; 428/233; 428/238; 428/240; 428/246; 428/283; 428/284; 428/286; 428/402; 428/913
[58] Field of Search ....................... 264/115, 116, 140; 128/284, 286, 288; 428/137, 195, 198, 240, 246, 284, 283, 286, 402, 511, 913, 304.4, 138, 233, 238

[56] References Cited

U.S. PATENT DOCUMENTS

| | | | |
|---|---|---|---|
| 3,950,219 | 4/1976 | Levesque | 264/121 |
| 4,018,951 | 4/1977 | Gross | 128/285 |
| 4,117,184 | 9/1978 | Erickson et al. | 428/913 |
| 4,293,609 | 10/1981 | Erickson | 428/246 |

*Primary Examiner*—James J. Bell

[57] ABSTRACT

A method of preparing fibrous hydrophilic fluff having increased absorbency is disclosed wherein an absorbent hydrophilic composite is mechanically disintegrated, either singly or in combination with a base fluffing material.

22 Claims, No Drawings

ABSORBENT POLYMER-FIBER COMPOSITES AND METHOD FOR PREPARING THE SAME

BACKGROUND OF THE INVENTION

This invention relates to fibrous hydrophilic fluff and a method of preparing said fluff wherein flexible absorbent laminates, either singly or in combination with a base fluffing material are disintegrated and mechanically worked into a fibrous fluff having a high water absorption capacity and absorption rate. There are numerous disposable articles in the form of diapers, tampons and the like available on the market which contain a central matrix of absorbent fibrous fluff having varying degrees of absorbency. There are, as well, a large variety of disposable absorbent pads used in institutions such as hospitals including underpads as well as adult and junior diapers. For example, U.S. Pat. No. 3,888,257 illustrates a disposable absorbent article utilizing a powdered polymer dispersed in a wicking substrate useful for the same general purposes as the articles which contain the absorbent hydrophilic fluff of this invention.

The conventional fluff matrix construction of the known prior art was fibrous fluff which had been treated with finely divided powdered absorbent polymer. In this regard, it has been found that application of the powdered absorbent polymer presented special problems of distribution within the cell matrix, as well as special problems in application. The finely divided powder is very difficult to maintain in anhydrous form while applying it to the fibrous fluff matrix. Presently, the accepted industry practice is to construct a substantially closed system of application in order to minimize the particulate dust which would emanate from the application site. Elaborate systems have been designed for the purpose of containing the absorbent particle dust, yet even a small amount of absorbent powder escaping from the substantially closed system requires special clean-up and maintenance procedures. When the powdered absorbent of the known prior art came in contact with moisture in the plant's atmosphere, it immediately began to swell, thereby yielding a gel which was not easily cleansed away due to its water absorbent properties. Thus, special solvents were required to maintain the equipment and, more significantly, the surrounding area in which the powdered absorbent dust settled. Fiberized wood pulp alone is not highly efficient. In order to enhance the absorbency of the fiberized wood pulp, water absorbent polymers have been proposed for distribution within the absorbent matrix.

SUMMARY OF THE INVENTION

Hydrophilic absorbent composites can be mechanically disintegrated and worked, either singly or in combination with a base fluffing material, to yield a fibrous hydrophilic fluff of enhanced absorbency and in which an absorbent polymer is substantially evenly distributed throughout the fibrous fluff matrix. The fibrous fluff matrix exhibits an enhanced resistance to separation of polymer from the fibrous fluff.

That hydrophilic absorbent fluff is characterized by being rapidly wetted and swelled by water and comprises a lightly cross-linked carboxylic polyelectrolyte in the form of a film/tissue composite which has been intimately distributed within the fibrous matrix by mechanical means.

Further, the present invention comprises a water swellable absorbent which is a composite fluffing of absorbent composite and base fluffing material. The base fluff material can be selected from a group of those articles which contain a fiber matrix capable of being mechanically disintegrated and worked into a fluff. The fluff base material may include the more common fluff pulp board which can be mechanically worked to prepare a fiberized wood pulp.

DETAILED DESCRIPTION OF THE INVENTION

For the purposes of this invention the following terms have been given the prescribed meaning. By "fluff" is meant a matrix of discontinuous wicking fibers having a plurality of zones wherein the absence of fibrous matter imports air pockets with varying degrees of uniformity thus producing a loose, soft mass of fibers.

By "absorbent fluff" is meant any absorbent matrix which has been prepared by disintegration and mechanically working absorbent composite and base fluffing material in accordance with the present invention.

By "base fluffing material" is meant a compacted mass of fibrous material which, when mechanically worked, is capable of forming a loose, soft mass of fibers herein defined as fluff.

Suitable hydrophilic absorbent composites which may be used in accordance with the practice of this invention includes all absorbent composites containing polymeric absorbents whereby the absorbent film, powder, print or saturation is adhered to one or more layers of wicking substrates such as tissue paper, crepe paper, paper wadding, paper toweling, woven fabrics, nonwoven fiber mats, cellulose fluff, polymeric foams, whether the wicking substrate is attached to one or both sides of the polymeric absorbent. Especially well adapted are those composites disclosed by Erickson et al., U.S. Pat. No. 4,117,184; Herring, U.S. Pat. No. 4,176,667; and Erickson, U.S. patent application Ser. No. 164,644, filed June 30, 1980 now U.S. Pat. No. 4,293,609.

Absorbent film laminates useful in the practice of this invention generally contain a layer of lightly cross-linked hydrophilic polymer film which has been placed on one or between two or more layers of wicking substrates.

The water-swellable or lightly cross-linked hydrophilic polymers useful in this invention can be any of the known hydrophilic polymers that can be constructed in a composite of polymeric absorbent and fibrous absorbent. Examples of such polymers are disclosed in U.S. Pat. Nos. 3,997,484; 3,926,891; 3,395,099; 4,090,013; and 4,190,562. In addition, examples of film laminates which incorporate the lightly cross-linked polymers of the above described examples are found in U.S. Pat. Nos. 4,117,184; 4,176,667; and Erickson, U.S. patent application Ser. No. 164,644, filed June 30, 1980.

The preferred hydrophilic polymers useful in this invention are polyelectrolytes exemplary of which are ammonium or alkali metal salts of homopolymers of acrylic or methacrylic acid and copolymers with one or more ethylenically unsaturated comonomers.

Preferably, the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl group has from 1 to 4 carbons.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono- or polycarboxylic acids. Examples of monocarboxylic acids include acrylic acid, methyacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows: acrylic acid-acrylate copolymers; acrylic acid-acrylamide copolymers; acrylic acid-olefinic copolymers; polyacrylic acid; acrylic acid-vinyl aromatic copolymers; acrylic acid-styrene sulfonic acid copolymers; acrylic acid-vinyl ether copolymers; acrylic acid-vinyl acetate copolymers; acrylic acid-vinyl alcohol copolymers and copolymers of methacrylic acid with all the above comonomers.

Illustrative examples of the polyfunctional cross-linking agents useful in this invention to convert the above polyelectrolytes into water-swellable polymers are set forth in U.S. Pat. Nos. 2,926,154; 3,224,986; and 3,332,909. These polyfunctional cross-linking agents are generally known as polyamide-polyamine epichlorohydrin adducts. The disclosure of these references are incorporated herein by reference. Similar cross-linking agents are also commercially available from Hercules Incorporated as Kymene 557 and Polycup 172. The structure of these adducts has been discussed in an article by M. E. Coor et al., *Journal of Applied Polymer Science*, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as cross-linking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction media containing 20 to 90 percent water, lower alcohols such as methanol or ethanol, or in aqueous solutions of the lower alcohols. The amino-epihalohydrin adducts are used directly as made without separation or concentration. The preparation and use of amino-epihalohydrin adducts as cross-linking agents is further disclosed in the patent application by J. R. Gross, Ser. No. 219,072 filed Dec. 22, 1980. This application is incorporated by reference herein.

Sulfonium zwitterions are known from U.S. Pat. Nos. 3,660,431; 3,749,737; and 3,749,738. The disclosure of these patents are incorporated herein by reference.

These cross-linking agents are used in an amount from about 0.05 to about 5.0 percent based on the weight of the polyelectrolyte used. This is generally sufficient to cause the polyelectrolyte to become lightly cross-linked.

Other hydrophilic polyers may also be employed, such as acrylic copolymer and starch/graft copolymers. Composites containing such polymers with wicking substrates are available commercially as Permasorb Sheet Laminate and Sanwet 1M-300. Also useful are the water-insoluble alkali salts of saponified, gelatinized starch/polyacrylonitrile graft polymers taught in U.S. Pat. Nos. 3,997,484 and 4,405,387. Other such polymers will be known.

The polymer can be in the form of a powder, flake, film or any other form and should be at least partially, preferably completely, adhered to at least one wicking substrate.

The composites can be prepared by laminations or other known techniques. For example, the noted polyelectrolytes in film form can be laminated between two sheets of tissue by the procedure taught in U.S. Pat. Nos. 4,117,184 and 4,076,673. One preferred laminate is prepared according to the former patent having a polymer film to tissue in a weight ratio of 1:1. When processed according to the present invention, the resulting fluff has that same ratio with the polymer uniformly dispersed with and substantially adherent to the tissue fibers.

The method of this invention is easily carried out by disintegrating the substantially dry composite in known devices, such as a hammer mill. The severity of the applied stress and the mechanical parameters are readily adjusted to optimum with simple preliminary experiments.

An optional embodiment available with the method is the concurrent disintegration of an absorbent composite and a base fluffing material. In that instance, it is only necessary that the composite and base fluffing material be added to the disintegrator in whatever predetermined ratio is desired in the resulting fluff. This option permits an easy adjustment of the amount of wicking substrate in the final fluff and can be achieved without shutting down the apparatus. The option also maximizes the fluid absorbent properties of both the fiberized base fluffing material and the fiberized hydrophilic absorbent laminate, and it does so in a way which yields a surprisingly high uptake of liquid in a solidified or gelled form. The composite fluff exhibits a high absorption capacity, in economical fashion. In this regard, as indicated above, the distribution of hydrophilic absorbent polymer within the absorbent matrix, unlike that of the known prior art, is accomplished in a uniform, intimately dispersed manner.

The resulting fluff is well suited for use in known absorbent devices. The fluff may be blended with other fluff or may be employed in a layered structure with fibrous fluff.

The method of this invention permits production of fluff having an absorbent polymer bonded to fibers of the fluff and being uniformly distributed throughout the fluff. The method permits quick and easy adjustment of the ratio of absorbent polymer to fibrous fluff. The method minimizes the amount of polymer lost during preparation as is a common problem in the use of granular polymers added to a fluff. The method is well adapted to use with soft flexible composites as well as relatively stiff off specification material.

Also within the scope of the present invention is the use of one or more layers of absorbent fluff in combination with a surrounding zone of fibrous fluff. The surrounding zone of fibrous fluff may or may not contain an absorbent polymer material which would enhance the absorbent properties of the fluff. The use of such fibrous fluff in the surrounding zones is dependent upon the manufacturer's specifications and desired absorption properties of the resultant absorption device. One embodiment for making such an absorbent device employs the method of this invention with the resulting fluff being intermittently deposited on a moving layer of fluff from a base fluffing material.

The following examples are presented to further illustrate, but not limit the scope.

EXAMPLE 1

A sandwich of tissue-absorbent was prepared according to the procedure of Example 9 in U.S. Pat. No. 4,117,184. This composite structure was then subjected to calendering as described in Erickson, U.S. patent application Ser. No. 164,644, filed June 30, 1980. The calendered composite had a relatively slow absorbing rate and good absorbent capacity. The composite was divided into small sections about 3×3 inches and placed into the container of a Waring blender. The composite was ground for 10 seconds at high speed which resulted in the composite being separated into a low density high bulk product resembling cellulose fluff pulp. The ground or fluffed composite showed an exceptionally high absorption rate and equal or greater absorption capacity compared with the unground composite. Data are shown in Table I.

EXAMPLE 2

The same procedure using similar laminate was followed except the calendered composite had a fast absorbency rate. Data are reported in Table I.

EXAMPLE 3

The composite laminate was the same as that used in Example 2 except that it was not calendered. The absence of calendering caused the film laminate to be substantially continuous before grinding. Therefore, after 10 seconds of grinding the tissue portion of the composite was not as thoroughly separated into a fibrous fluff mass as in Example 2; see Table I.

EXAMPLE 4

The same as the composite structure of Example 3 except the absorbent composite is perforated by punching holes, one-quarter inch on centers with 0.090 inch (0.23 cm) needles. Perforation is accomplished by running the composite between a roll containing the needles and a rubber back-up roll. See Table I.

EXAMPLE 5

The same as the composite structure of Example 1 except the tissue is applied to only one side of the absorbent film. Thus, in Example 5 the ratio of tissue to absorbent polymer film is approximately 1 tissue to 2 film by weight. See Table I.

Example 6 proved an unexpected result; and is presented for comparison.

EXAMPLE 6

An absorbent polymer composition was formulated as follows:

|  | Parts Solids by Weight |
| --- | --- |
| Acrylic copolymer solution | 94.2 |
| Polyoxyethylene sorbitan mono-laurate | 5.0 |
| Amide/epichlorohydrin polymer | 0.8 |

Deionized water was added to obtain a 20 percent solids composition to reduce viscosity. The ingredients were thoroughly mixed, with air introduced to provide air pockets in the final film.

Cellulose fibers were obtained from the absorbent filler of a "Kimbies" (Kimberly Clark) baby diaper. Thus, 56.1 grams of these fibers were mixed with 56.1 grams solids of the above composition using a Hobart mixer and mixing for 15 minutes. The wet fiber cake was spread on a preheated, release coated glass plate and dried in a forced hot air oven for 30 minutes at 250° F. (121° C.). The dry mixture was ground in a Waring blender for 15-20 seconds as previously stated in the other examples. This procedure produced only a high density powder and no lofting or high bulk composite. The absorbency rate of the powder was very slow and the absorbent capacity was very low. See Table I.

Similar results to Examples 1-5 are obtained when the absorbent composite employed in the procedures of these examples is a laminate sold commercially as Permasorb No. 28-7160; water-insoluble salts of saponified, gelatinized starch/polyacrylonitrile graft copolymers; copolymers of acrylic esters and acids with starch.

For the purposes of the above-described invention, a fluffing chamber which yields the change in physical form of base fluffing material and absorbent laminate may be any one of a number of mechanical devices including, but not limited to, grinders, hammer mills, ultrasonic vibration, fibrillations, etc.

TABLE I

| ABSORBENCY RATE AND CAPACITY OF GROUND TISSUE/FILM COMPOSITES | | | | |
| --- | --- | --- | --- | --- |
|  | Laminate Form | | Ground Form | |
| Example | Rate (seconds) | Capacity (grams/grams) | Rate (seconds) | Capacity (grams/grams) |
| 1 | >100 | 26.4 | Instant | 32.0 |

TABLE I-continued

ABSORBENCY RATE AND CAPACITY OF
GROUND TISSUE/FILM COMPOSITES

| Example | Laminate Form | | Ground Form | |
|---|---|---|---|---|
| | Rate (seconds) | Capacity (grams/grams) | Rate (seconds) | Capacity (grams/grams) |
| 2 | 35 | 28.8 | Instant | 29.0 |
| 3 | <300 | 27.0 | <15 | 28.0 |
| 4 | 60 | 27.0 | >10 | 29.0 |
| 5 | <300 | 33.0 | <15 | 34.0 |
| 6 | — | — | >60 | 10.0 |

What is claimed is:

1. A method for preparing a fibrous fluff of improved absorbency, said method comprising the mechanical disintegration of a hydrophilic absorbent composite which comprises a layer of a swellable hydrophilic polymer and one or more substrates of wicking material at least partially bonded to said polymeric layers.

2. The method of claim 1 wherein said polymeric layer is a continuous substantially uniform film.

3. The method of claim 1 wherein said composite is perforated.

4. A method of claim 1 wherein said layer of said polymer comprises a substantially discontinuous and crushed film.

5. A method of claim 4 wherein said layer is an aerated film having a density rate of from about 1.1 to about 0.3 grams per cubic centimeter.

6. A method of claim 1 wherein said layer of polymer is in particulate form.

7. A method of claim 6 wherein said layer is a granular powder.

8. A method of claim 6 wherein said layer is a flaked polymer.

9. A method of claim 1 wherein said polymer is a lightly cross-linked carboxylic polyelectrolyte.

10. A method of claim 9 wherein said layer is a cracked and aerated film having a density of from about 1.1 to 0.3 grams per cubic centimeter.

11. A method of claim 1 wherein said polymer is a copolymer of alkyl acrylates and acrylic acid with starch.

12. The method of claim 1 wherein said wicking substrate layers are selected from the group consisting of woven fabrics, paper tissues, nonwoven fiber mats and polymeric foams.

13. The method of claim 12 wherein said polymeric foam is a polyurethane foam.

14. A method of making a fibrous fluff blend wherein the disintegrated composite of claim 1 is combined with uncoated base fluffing material.

15. The method of claim 14 which comprises passing said composite through a zone wherein the composite is mechanically combined during disintegration with base fluffing material into a composite-base fluffing material blend.

16. The method of claim 15 wherein 1 to 99 percent by volume of absorbent composite is combined with 99 to 1 percent by volume of base fluffing material.

17. The method of claim 14 wherein said fluffing material is disintegrated, formed into a moving layer, said composite is disintegrated and deposited on a moving layer of said base fluffing material.

18. The method of claim 17 wherein the disintegrated composite is deposited at periodic intervals on said moving layer.

19. The absorbent fluff prepared according to the method of claim 1.

20. An absorbent device which comprises the absorbent fluff of claim 19, one or more layers of intermediate wicking sheets, a water-impermeable back sheet and a water-permeable face sheet.

21. The absorbent device of claim 20 wherein said water-impermeable back sheet is polyethylene and said face sheet is a nonwoven fiber sheet or porous paper.

22. The absorbent device of claim 20 wherein said water-permeable face sheet is a perforated polymer film.

* * * * *